United States Patent [19]

Smith

[11] Patent Number: 4,954,264

[45] Date of Patent: Sep. 4, 1990

[54] APPARATUS FOR SEPARATING MONONUCLEAR CELLS FROM BLOOD AND METHOD OF MANUFACTURING AND USING THE SAME

[75] Inventor: Ward C. Smith, Mahwah, N.J.

[73] Assignee: Becton-Dickinson and Company, Franklin Lakes, N.J.

[21] Appl. No.: 305,953

[22] Filed: Feb. 2, 1989

[51] Int. Cl.⁵ .................. B01D 33/02; B04B 3/00; A61K 35/14
[52] U.S. Cl. .................. 210/782; 210/767; 210/789; 424/529; 424/532; 424/534; 435/2; 435/287; 435/296
[58] Field of Search .................. 435/2; 424/101; 210/789, 782, 767

[56] References Cited

U.S. PATENT DOCUMENTS

| | | |
|---|---|---|
| 3,852,194 | 12/1974 | Zine, Jr. . |
| 3,920,549 | 11/1975 | Gigliello et al. . |
| 3,945,928 | 3/1976 | Ayres . |
| 3,960,727 | 6/1976 | Hochstrasser . |
| 4,101,422 | 7/1978 | Lamont et al. . |
| 4,147,628 | 4/1979 | Bennett et al. . |
| 4,153,739 | 5/1979 | Kessler . |
| 4,190,535 | 2/1980 | Luderer et al. . |
| 4,255,256 | 3/1981 | Ferrante et al. ......... 210/789 |
| 4,255,256 | 3/1981 | Ferrante et al. . |
| 4,295,974 | 10/1981 | Cornell .................. 210/789 |
| 4,310,430 | 1/1982 | Ichikawa et al. . |
| 4,350,593 | 9/1982 | Kessler . |
| 4,417,981 | 11/1983 | Nugent . |
| 4,435,293 | 3/1964 | Graham, Jr. et al. . |
| 4,436,631 | 3/1984 | Graham, Jr. et al. . |
| 4,457,782 | 7/1984 | Honda et al. . |
| 4,487,700 | 12/1984 | Kanter . |
| 4,534,798 | 8/1985 | Honda et al. . |
| 4,640,783 | 2/1987 | Carroll et al. . |
| 4,640,785 | 2/1987 | Carroll et al. ......... 210/789 |
| 4,751,001 | 6/1988 | Saunders . |
| 4,816,168 | 3/1989 | Carrol et al. . |
| 4,818,418 | 4/1989 | Saunders . |
| 4,824,560 | 4/1989 | Alspector ............. 210/789 |
| 4,844,818 | 7/1989 | Smith . |

FOREIGN PATENT DOCUMENTS 1127537 7/1982 Canada .
0036168 9/1981 European Pat. Off. .

OTHER PUBLICATIONS

Boyum–Chemical Abstracts, vol. 69 (1968), p. 9265X.
Experimental Cell Research, Splinter et al., Biochimica Et Biophysics Acta, Elsevier Science Publishers BV, 1984, pp. 159–168.
Iodinated Density Gradient Media, by Dr. D. Rickwood, IRL Press.
Rapid, Quantitative Human Lymphocyte Separation And Purification In a Closed System, by Luderer et al., Molecular Immunology, 16, pp. 621–624 (1979).
Comparison of T and B Cell Analyses on Fresh and Aged Blood, J. K. A. Nicholson et al., pp. 29–40, 1984.

Primary Examiner—Sam Rosen
Attorney, Agent, or Firm—Hoffmann & Baron

[57] ABSTRACT

A device for separating mononuclear cells from blood includes a collection tube, a first layer of a liquid density gradient material placed in the tube, a second layer of a gel-like substance placed in the tube and situated above the first layer, a porous foam member placed in the tube and situated above and in contact with the second layer of gel-like substance, and a third layer of a Newtonian gel-like substance placed in the tube above the porous foam member. The gel-like substance of the second layer has a lower specific gravity than that of the liquid density gradient material of the first layer so that it floats on top of the first layer. The gel-like substance of the second layer becomes less viscous when heated such that it is absorbed by the porous foam member and forms a hydraulic barrier between the liquid density gradient material of the first layer and a blood sample placed in the collection tube.

41 Claims, 1 Drawing Sheet

APPARATUS FOR SEPARATING MONONUCLEAR CELLS FROM BLOOD AND METHOD OF MANUFACTURING AND USING THE SAME

BACKGROUND OF THE INVENTION

1. Field of The Invention

This invention relates to the separation of mononuclear cells from whole or diluted blood, and more particularly relates to a blood separation device and a method of manufacturing the device and of separating blood components using such a device.

2. Description of the Prior Art

A well known blood separation device on the market today includes a blood collection tube containing an aliquot of a Newtonian gel and an aliquot of a liquid density medium, such as Ficoll-Paque (TM). The Newtonian gel acts as a barrier between the liquid density medium and a sample of blood placed in the tube atop the gel. When the tube is centrifuged, the liquid density medium acts to separate the mononuclear cells from the other blood components.

The conventional blood separation device described above works well for clinical laboratory applications, where a blood sample is placed in the tube and immediately centrifuged to separate out the targeted blood components. The device is not intended for use as, nor can it function as, a shippable blood separation device, i.e., such as where the physician draws a blood sample into the collection tube and sends it to a laboratory for centrifugation or further processing.

The reason why such devices cannot be shipped is that both the gel and the density medium are essentially liquids and will not retain their pre-processed positions in the tube. Although each is immiscible with respect to the other, they will run in the tube when the tube is placed on its side. Accordingly, when the device is in such a position or if the device is disturbed, the Newtonian gel may no longer be in position between the liquid density medium and a blood sample contained in the tube, and thus may no longer act as a barrier between the two. The blood sample will mix with the liquid density medium and may affect its blood separation characteristics, namely its specific gravity or density, and consequently its ability to properly separate the mononuclear cells from the other components of the blood sample.

OBJECTS AND SUMMARY OF THE INVENTION

It is an object of the present invention to provide a blood separation device which is shippable.

It is another object of the present invention to provide a method for separating the mononuclear cells from the other components of a blood sample.

It is yet another object of the present invention to provide a method for making a shippable blood separation device.

It is a further object of the present invention to provide a blood separation device and method for using the same which overcomes the inherent disadvantages of known separation devices, such as that described previously.

In accordance with one form of the present invention, a blood separation device, and in particular one which is adapted for separating mononuclear cells from whole or diluted blood, includes a collection tube having a bottom end which is closed and an opposite top end which is open for receiving a blood sample. The collection tube is adapted to be centrifuged.

The device further includes a first layer of a liquid density gradient medium, situated at the closed end of the tube, a relatively thin second layer of a lightweight (that is, low density) gel placed on top of the first layer of liquid density gradient medium, a porous foam member situated on top of and in contact with the second layer of low density gel, and, in a preferred embodiment, a third layer of a Newtonian gel disposed above the porous foam member.

The second layer of low density gel is preferably a grease or a petrolatum, for example, a petroleum jelly, such as that commonly referred to by the trademark Vaseline, which has a specific gravity which may be less than 1 (or is at least less than the specific gravity of the liquid density separation medium) so that it floats on top of the first layer of liquid density separation medium. Even more preferably, the viscosity of the second gel layer changes with temperature so that the gel has a low viscosity at higher temperatures and a higher viscosity at lower temperatures.

The porous foam member has an open cellular structure. It is effectively transparent to the red blood cells and other heavier components, for example, the granulocytes, of the blood sample, which will migrate downwardly and pass through the foam member during centrifugation of the blood separation device, but will act as a barrier to the Newtonian gel layer, which is much thicker (i.e., more viscous). The porous foam member also acts as a wick to the petroleum jelly second layer, which flows into the lower surface of the porous foam member, especially at elevated temperatures when the jelly is less viscous.

The second layer of gel (for example, the petroleum jelly) acts as a partition between the blood sample and the liquid density gradient material by sealing the porous foam member prior to centrifugation. In this way, the blood sample will not affect the blood separation characteristics, such as the specific gravity, of the liquid density gradient material, even when the collection tube is placed on its side after blood is drawn and during shipment to a clinical laboratory for processing.

In accordance with a method of using the blood separation device of the present invention, a sample of blood is introduced into the device having the structure described previously. The collection tube is centrifuged at a rate of about 1,000 to about 2,000 G's for about 15 to about 30 minutes.

Prior to centrifugation, the components of the blood separation device assume the following positions: the first layer of liquid density gradient material is situated at the bottom of the closed end of the collection tube; the second layer of low density gel, such as petroleum jelly, resides on top of the first layer; the porous foam member is disposed on top of the second layer of petroleum jelly and in contact with the jelly so that the jelly will be at least partially absorbed by the porous foam member; and the third layer of Newtonian gel (if used) is situated above the porous foam member. An additional empty space is provided in the collection tube above the Newtonian gel layer to accomodate a blood sample as well as a stabilizing reagent or an anti-coagulant, if desired.

Prior to centrifugation of the collection tube, the "greased" porous foam member, that is, containing the petroleum jelly second layer, acts as a barrier and maintains the separation between the blood sample or the stabilizing reagent or anti-coagulant, and the liquid density separation material of the first layer so that the two will not intermix and affect the blood separation characteristics of the liquid density gradient material.

During centrifugation of the collection tube, the red blood cells will pass through the porous foam member as well as the petroleum jelly second layer contained in it, and the liquid density gradient material (or the Newtonian gel if used) assumes a position in the tube between the mononuclear cells and the heavier components of the blood sample.

The plasma which has separated from the blood may be removed by using a pipette, leaving the mononuclear cell fraction containing platelets, lymphocytes and monocytes. The mononuclear cells are then removed by adding a diluent after the plasma has been removed to form a suspension disposed atop the layer of Newtonian gel, which suspension is then removed by using a pipette.

Furthermore, in accordance with a method of manufacturing the blood separation device described previously, an aliquot of liquid density separation material is placed in the bottom closed end of a collection tube to form a first layer. Directly on top of the first layer of liquid density separation medium is placed a second layer of a gel, preferably a petroleum jelly, which gel may have a specific gravity of less than 1. Accordingly, the gel will float on top of the first layer of liquid density separation material, but will not affect the density and separation characteristics of the liquid density separation material.

A porous foam member having an open cellular structure is then placed in the collection tube and situated in contact with the petroleum jelly layer. A Newtonian gel may then be added to the collection tube and is disposed on top of the porous foam member.

The second layer of gel (i.e., the petroleum jelly layer) is preferably selected so that it has a low viscosity at high temperatures and a high viscosity at lower temperatures. In other words, during the initial placement of the second gel layer into the collection tube at, for example, room temperatures, the second layer will be less flowable and will not coat the sides of the collection tube.

However, when the collection tube is heated, such as during autoclaving, the petroleum jelly layer will become more viscous and will readily flow into and be absorbed by the porous foam member to a depth which may be equal to the height of the second layer. In this manner, the petroleum jelly layer will be retained by the porous foam member, and the "greased" foam member will act as a barrier between a blood sample placed in the collection tube, or, if desired, a stabilizing reagent or anti-coagulant, and the liquid density separation medium of the first layer.

The second layer of gel (for example, the petroleum jelly or grease) is placed in the collection tube independently of the porous foam member. If the petroleum jelly or grease were applied to the porous foam member before placing the member in the collection tube, the jelly would smear the sides of the collection tube as the foam member is placed in the tube, making an unsightly product. This is avoided in the present invention.

These and other objects, features and advantages of this invention will become apparent from the following detailed description of illustrative embodiments thereof, which is to be read in connection with the accompanying drawings.

DETAILED DESCRIPTION OF THE PREFERRED EMBODIMENTS

Figure 1:
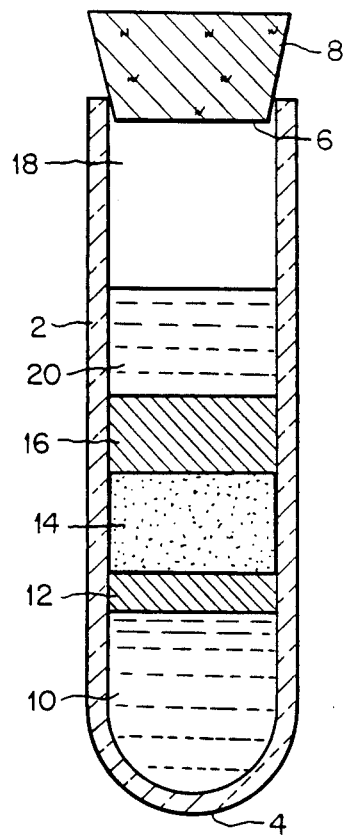
FIG. 1 is a longitudinal cross sectional view of a blood separation device formed in accordance with one form of the present invention, prior to autoclaving or heating the device.

Referring initially to FIG. 1 of the drawings, it will be seen that a blood separation device constructed in accordance with one form of the present invention includes a collection tube 2, which may be in the form of a test tube, having a closed bottom end 4 and an opposite open top end 6. The open top end 6 may be fitted with a removable stopper 8 or other closure, which closure is pierceable with a needle so that a blood sample may be added to the collection tube. Additionally, the collection tube 2 may be evacuated to allow blood to be drawn from the patient directly into the tube.

The blood separation device of the present invention, in the form illustrated by FIG. 1, employs a first layer 10 of a liquid density gradient material. The first layer 10 is situated at the bottom closed end 4 of the collection tube. The liquid density gradient material of the first layer 10 may be, for example, Ficoll-Paque (TM). The liquid density gradient material is selected to have a specific density of between about 1.065 and about 1.100, depending upon whether a layer of a Newtonian gel-like substance is used, so that it will assume the proper position between the mononuclear cells and the heavier components of a blood sample after the collection tube 2 is centrifuged, as will be explained.

A second layer 12 of material is placed on top of the first layer 10. The second layer 12 is a low density gel, that is, having a specific gravity of between about 0.8 and about 1.1, and preferably about 1.05. With a specific gravity as described above, the second gel layer 12 will essentially "float" on top of the liquid density gradient material, which has a greater specific gravity. This facilitates the manufacture of the blood separation device and eliminates the need for pre-spinning the device as is required in many conventional blood separation devices.

The preferred gel of the second layer 12 is in the form of a petroleum jelly or grease, for example, that which is commonly referred to by the trademark Vaseline (TM). Alternatively, a material having a higher polymer structure than a Vaseline jelly and which is also hydrophobic may be used.

It is also advantageous to use a gel as the second layer 12 which is more viscous at lower temperatures and less viscous and more flowable at higher temperatures, as will be explained. The second layer 12 of gel may be relatively thin, that is, for a 10 ml collection tube, a 0.2 ml quantity of gel may be sufficient.

On top of the second layer of gel is placed a porous foam member 14. The porous foam member 14 has an open cellular structure, and may be formed from a reticulated urethane foam. With this structure, the member is effectively transparent to the blood cells, that is, it allows the red blood cells of the blood sample to pass through it during centrifugation of the blood separation device.

The porous foam member 14 also acts as a structure to contain the thin layer of petroleum jelly (i.e., the second layer 12). The porous foam member is placed in contact with the second layer of gel, which gel will flow into and be retained by the porous foam member when the gel is heated to become sufficiently flowable, such as during autoclaving. The gel of the second layer 12 will penetrate the porous foam member 14 to a depth which may be approximately equal to the height of the layer of gel. For this reason, only a small quantity of gel is needed, that is, just enough to fill the lower portion of the porous member and seal the member.

The blood separation device may further include a third layer 16 of a Newtonian gel-like substance, which layer is placed on top of the porous foam member 14. The Newtonian gel has a specific gravity of between about 1.065 and about 1.085, more preferably between about 1.075 and about 1.08, and most preferably about 1.077, so that it will assume a proper position between the mononuclear cell fraction containing platelets, lymphocytes and monocytes and the heavier components of the blood sample after centrifugation.

If the third layer 16 of Newtonian gel is used in the device, then the specific gravity of the liquid density gradient material of the first layer 10 should be between about 1.08 and about 1.100, more preferably between about 1.085 and about 1.095, and most perferably about 1.09. If the third layer 16 of Newtonian gel is not used, then the specific gravity of the liquid density gradient material may be that stated previously for the Newtonian gel.

The collection tube 2 is of sufficient size to define a free space 18 above the third layer 16 of Newtonian gel. This space is, of course, provided to receive a sample of blood.

If desired, an anti-coagulant or a stabilizing reagent 20 may be added to the blood separation device. The use of a stabilizing reagent, preferably in a 1:1 dilution with respect to a blood sample, allows overnight shipment of the blood sample in the blood separation device to a reference laboratory without sample degradation, prior to separation using the same collection tube 2. The stabilizing reagent 20 may include a culture medium, which tends to feed the cells and maintain their viability, if longer storage or shipment times are required, or an anti-coagulant.

The stabilizing reagent 20 which may be used may typically be an isotonic or hypertonic solution, an ionic solution having a high molecular weight with organic molecules added, cell culture media such as RPMI 1640, and McCoy's medium. The stabilizing reagent is of a volume which is consistent with blood dilution ratios of from about 0.25:1 to about 3:1 of stabilizing reagent to blood.

Figure 2:
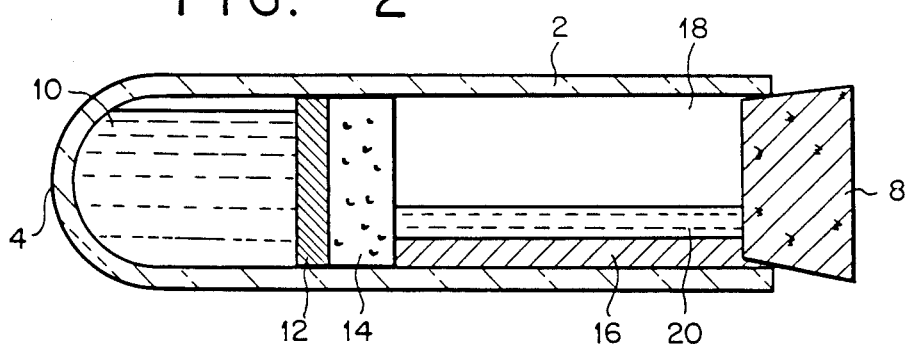
FIG. 2 is a longitudinal cross sectional view of the blood separtion device of FIG. 1 and the position of the components thereof when the device is placed on its side, and after autoclaving.

FIG. 2 illustrates the blood separation device of the present invention positioned on its side during storage or shipment. The porous foam member 14, now "greased" with the absorbed second layer 12 of gel (for example, petroleum jelly) maintains the first layer 10 of liquid density gradient material in the bottom closed end 4 of the collection tube, as the liquid density gradient material cannot penetrate the greased porous foam member.

Similarly, it is noted from FIG. 2 that the Newtonian gel 16 has slumped or run partially lengthwise in the collection tube such that the anti-coagulant or stabilizing reagent 20, which is a liquid, comes into contact with the porous foam member 14. However, the porous foam member containing the petroleum jelly acts as a hydraulic barrier and prevents contact between the stabilizing reagent (or the blood sample) and the liquid density gradient material 10 which otherwise might have affected the blood separation characteristics, such as the density, of the liquid density gradient material. Although the stabilizing reagent or blood sample may enter the pores of the foam member, it will still not come in contact with the liquid density gradient material due to the grease barrier provided by the second layer 12.

Figure 3:
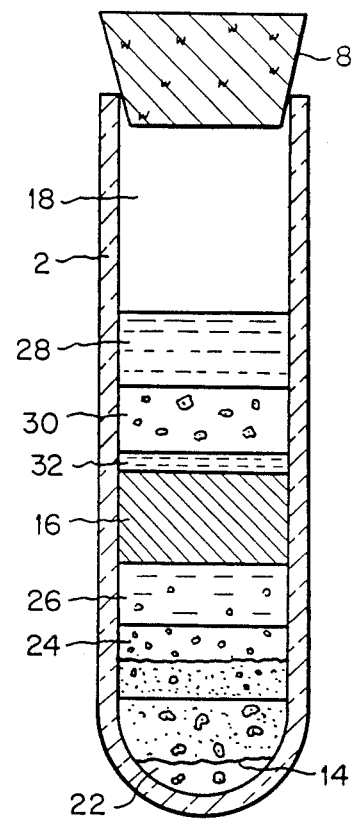
FIG. 3 is a longitudinal cross sectional view of the device of FIG. 1, illustrating the state of the blood components and other elements of the blood separation device illustrated by FIG. 1 after the device containing a sample of blood is centrifuged.

The blood separation device may be centrifuged at between about 1,000 and 2,000 G's (or possibly less than 1,000 G's if no Newtonian gel layer is used) for about 15 to about 30 minutes. Upon centrifugation, the blood components and the liquid density gradient material of the first layer 10 and the Newtonian gel of the third layer 16 assume the positions shown in FIG. 3. The red blood cells 22, or erythrocytes, which are generally the heaviest blood components, gravitate through the porous foam member toward the bottom closed end 4 of the collection tube. The red cells are followed by a layer of granulocytes 24. The porous foam member 14 has also moved downwardly in the collection tube and occupies a space generally near the bottom of the tube in the vicinity of or within the layers of granulocytes and red blood cells.

A heavy phase portion 26 of the liquid density separation medium, which phase includes some residual red cells which have not migrated to the bottom of the collection tube, resides generally above the granulocyte layer 24. The heavy phase of the liquid density separation medium is that portion which is substantially undiluted by the blood plasma.

The third layer 16 of Newtonian gel, if used, has assumed a position between the heavier components of the blood, such as the granulocytes and the red blood cells, and the plasma 28 of the blood and the mononuclear cell fraction 30 containing the platelets, lymphocytes and monocytes.

Disposed directly above the Newtonian gel layer 16 is a light phase 32 of the liquid density separation medium. The light phase is generally believed to be caused by the red cells carrying the water component of the blood into the layer 10 of the liquid density separation medium during centrifugation, which has the effect of diluting a portion of the liquid density medium such that its specific gravity is less than that of the Newtonian gel. The light phase 32 is displaced to a position above the Newtonian gel layer 16, and the mononuclear cells 30 reside directly above the light phase of the liquid density separation medium, and above the mononuclear cells is the blood plasma 28. The light phase 32 of the liquid density medium layer is desired because it acts to "buoy up" the mononuclear cells, which effect tends to minimize the loss of those cells by their sticking to or imbedding in the Newtonian gel layer 16. As a result, the cells are easily removed from the collection tube 2 after separation with little loss of cells.

The plasma 28 of the blood may be removed, care being exercised to avoid disturbing the mononuclear cell fraction 30 containing the platelets, lymphocytes and monocytes. This operation may be carried out by means of a pipette (not shown), leaving the platelets, lymphocytes and monocytes atop the Newtonian gel layer 16. Thereafter, a diluent, such as an isotonic $Ca+2$, $Mg+2$ - free salt buffer solution, is gently run into the collection tube onto the Newtonian gel layer. The tube may then be gently rocked or otherwise agitated to cause the platelets, lymphocytes and monocytes which had been resting on the Newtonian gel layer to be suspended in the buffer solution, and this suspension may then be removed from the tube by using a pipette (not shown) for further processing according to standard and well known procedures.

In accordance with the preferred method of manufacturing the blood separation device of the present invention, the first layer 10 of liquid density gradient material is placed in the bottom closed end 4 of the collection tube 2. On top of this layer is placed the second layer 12 of gel, preferably, a petroleum jelly, or grease. The porous foam member 14 is then placed in the collection tube on top of and in contact with the petroleum jelly layer 12. The third layer 16 of Newtonian gel is then added to the collection tube, followed by the stabilizing reagent 20, if desired.

At room temperature, the petroleum jelly or grease has a higher viscosity than it has at higher temperatures. As a result, the grease layer 12 will be less flowable and will not coat the sides of the collection tube when placed in the tube. Additionally, the petroleum jelly layer 12 has a specific gravity which is approximately less than 1 (or is at least less than the specific gravity of the liquid density separation medium) so that it floats on top of the first layer 10 of liquid density separation medium. Accordingly, it will assume its proper position above the liquid density separation medium layer when first placed in the collection tube during manufacture.

After the various layers of materials have been placed in the collection tube 2, the tube is then autoclaved. At autoclaving temperatures, the petroleum jelly layer 12 will be become less viscous and will readily flow into and be absorbed by the porous foam member 14 so that it coats at least the bottom portion of the porous foam member. The "greased" foam member 14 will act as a barrier between a blood sample placed in the collection tube or the stabilizing reagent 20, and the liquid density separation medium of the first layer 10. The method of manufacturing the blood separation device thus eliminates the need for pre-spinning the device as is required in many conventional blood separation devices.

Using a porous foam member in combination with a grease or gel to form a hydrophobic partition, as in the present invention, and manufacturing the blood separation device of the present invention as described above, is advantageous in a number of ways. It is difficult to handle a foam part that contains a gel or a grease. It is also difficult to position a viscous gel in the pores of a porous foam part. Furthermore, many greases and gels are light and could float upwards in the device during use and interfere with cell removal.

Accordingly, in the preferred form of the present invention, the blood separation device utilized a grease which has the required relatively high viscosity at room temperature and has a low viscosity at higher temperatures to give hydrophobicity to the seal or barrier thus formed. The second layer 12 of petrolatum resides on top of the first layer 10 of the liquid density medium and, when the foam member 14 is placed in contact with the petrolatum, moves into the foam member to a depth substantially equal to the height of the petrolatum layer. The petrolatum cools to form a structural seal.

Application of the grease or petrolatum to the porous foam member 14 before placing the member in the collection tube 2 would smear the grease on the sides of the tube, making an unsightly product. Also, by having the grease or petroleum jelly contained in the pores of the foam member 14 offers a less tendency for the grease to migrate in the separation device at melting temperatures due to capillary forces within the foam member.

The Newtonian gel which is placed on top of the foam member 14 cannot enter the pores of the foam member due to its high viscosity. When the device is stored on its side, as illustrated by FIG. 2, the Newtonian gel will slump, exposing the surface of the porous foam member 14 to the blood sample or the liquid stabilizing reagent 20. The stabilizing reagent may saturate the porous foam, but cannot contact the layer 10 of liquid density medium due to the grease barrier formed in the porous foam member.

The blood separation device of the present invention with a 1:1 dilution of stabilizing reagent and whole blood will allow a shipping period of 24 hours before cell separation. This is sufficient time for a physician to ship the device with a sample of blood to a reference laboratory for separation and testing. The present invention thus allows a physician to do a minimum number of steps in obtaining test results, as the device does not require centrifugation in the physician's office.

Alternatively, the stabilizing reagent 20 may be omitted from the blood separation device and added on use at the reference laboratory so that the device can be used with whole blood alone. While the stabilizing reagent offers shipability and better percent yields, this alternative design will work well for onsight applications.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. Apparatus for separating mononuclear cells from blood, which comprises:

a collection tube having a bottom closed end and an opposite open top end for receiving a blood sample, and being adapted to be centrifuged;

a first layer of a liquid density gradient medium contained in the collection tube and situated at the closed end of the tube;

a second layer of a gel-like substance contained in the collection tube and placed on top of the first layer of liquid density gradient medium, the second layer having a specific gravity which is less than that of the first layer so that it floats on top of the first layer; and a porous foam member contained in the collection tube and situated on top of and in contact with the second layer of gel-like substance;

the collection tube being of sufficient size to define a free space above the porous foam member to receive a blood sample;

the second layer of gel-like substance being adapted to coat a portion of the porous foam member with which it is contact to form a hydraulic barrier between a blood sample received by the tube and the first layer of liquid density gradient medium to prevent intermixing of the first layer and the blood sample prior to centrifuging the tube.

2. An apparatus as defined by claim 1, which further comprises a stabilizing reagent contained in the collection tube and situated above the porous foam member prior to centrifugation of the tube.

3. An apparatus as defined by claim 2, wherein the stabilizing reagent is one of an isotonic solution and a hypertonic solution.

4. An apparatus as defined by claim 2, wherein the stabilizing reagent is an ionic solution having a high molecular weight with organic molecules added.

5. An apparatus as defined by claim 2, wherein the stabilizing reagent is a cell culture media.

6. An apparatus as defined by claim 5, wherein the cell culture media is RPMI 1640.

7. An apparatus as defined by claim 2, wherein the stabilizing reagent is a McCoy's medium.

8. An apparatus as defined by claim 2, wherein the stabilizing reagent is of a volume which is consistent with blood dilution ratios of from about 0.25:1 to about 3:1 of stabilizing reagent to blood.

9. An apparatus as defined by claim 2, wherein the stabilizing reagent is in a 1:1 dilution with respect to a blood sample.

10. An apparatus as defined by claim 1, which further comprises an anti-coagulant contained in the collection tube and situated above the porous foam member.

11. An apparatus as defined by claim 1, wherein the collection tube is of a 10ml volume, and the second layer of gel-like substance is of a volume of about 0.2ml.

12. An apparatus as defined by claim 1, wherein the gel-like substance of the second layer is a petrolatum.

13. An apparatus as defined by claim 1, wherein the gel-like substance of the second layer is a petroleum jelly.

14. An apparatus as defined by claim 1, wherein the gel-like substance of the second layer has a specific gravity of between about 0.8 and about 1.1.

15. An apparatus as defined by claim 14, wherein the specific gravity of the gel-like substance of the second layer is about 1.05.

16. An apparatus as defined by claim 1, wherein the liquid density gradient medium of the first layer is selected to have a specific gravity of between about 1.065 and about 1.085.

17. An apparatus as defined by claim 1, wherein the liquid density gradient medium of the first layer is selected to have a specific gravity of between about 1.075 and about 1.08.

18. An apparatus as defined by claim 1, wherein the liquid density gradient medium of the first layer is selected to have a specific gravity of about 1.077.

19. An apparatus as defined by claim 1, wherein the liquid density gradient medium of the first layer is selected to have a specific gravity of between about 1.08 and about 1.100.

20. An apparatus as defined by claim 1, wherein the liquid density gradient medium of the first layer is selected to have a specific gravity of between about 1.085 and about 1.095.

21. An apparatus as defined by claim 1, wherein the liquid density gradient medium of the first layer is selected to have a specific gravity of about 1.09.

22. An apparatus as defined by claim 1, wherein the liquid density gradient medium of the first layer is FicollPaque (TM).

23. An apparatus as defined by claim 1, which further comprises closure means fitted onto the open top end of the collection tube.

24. An apparatus as defined by claim 1, wherein the free space defined by the collection tube is evacuated to allow the direct drawing of the blood sample.

25. An apparatus as defined by claim 1, which further comprises a third layer of a Newtonian gel-like substance contained in the collection tube and positioned above the porous foam member.

26. An apparatus as defined by claim 25, wherein the Newtonian gel-like substance of the third layer has a specific gravity of between about 1.065 and about 1.085.

27. An apparatus as defined by claim 25, wherein the Newtonian gel-like substance of the third layer has a specific gravity of between about 1.075 and about 1.08.

28. An apparatus as defined by claim 25, wherein the Newtonian gel-like substance of the third layer has a specific gravity of about 1.077.

29. An apparatus as defined by claim 25, which further comprises a stabilizing reagent contained in the collection tube and situated above the third layer of Newtonian gel-like substance.

30. An apparatus as defined by claim 25, which further comprises an anti-coagulant contained in the collection tube and situated above the third layer of Newtonian gel-like substance.

31. An apparatus as defined by claim 1, wherein the porous foam member is formed from a reticulated urethane foam.

32. An apparatus as defined by claim 1, wherein the second layer of gel-like substance is partially absorbed by the porous foam member.

33. An apparatus as defined by claim 32, wherein the second layer of gel-like substance is absorbed by the porous foam member to a depth in the porous foam member equal to about the height of the second layer.

34. A method of separating mononuclear cells from a sample of blood, which comprises the steps of:
introducing a sample of blood into a blood separation device, the device including a collection tube, a first layer of a liquid density gradient material contained in the collection tube, a second layer of gel-like substance contained in the collection tube and situated above the first layer, a porous foam member contained in the collection tube and situated above the second layer and in contact with the second layer, and a third layer of a Newtonian gel-like substance contained in the collection tube and positioned above the porous foam member, the second layer of gel-like substance being adapted to coat the portion of the porous foam member with which it is in contact and acting as a barrier between the first layer of liquid density gradient material and a blood sample introduced into the blood separation device, the third layer of Newtonian gel-like substance being formed with a specific gravity such that it is adapted to assume a position in the collection tube between the mononuclear cells and the heavier components of a blood sample placed in the tube after centrifugation of the tube; and centrifuging the collection tube such that the Newtonian gel layer assumes a position in the tube between the mononuclear cells and the heavier components of the blood sample.

35. A method as defined by claim 34, which further comprises the steps of removing plasma which has separated from the blood and adding a diluent to the mononuclear cells after the plasma has been removed to form a suspension disposed atop the layer of Newtonian gel-like substance.

36. A method as defined by claim 35, which further comprises the step of removing the suspension from atop the layer of Newtonian gel-like substance.

37. A method of separating mononuclear cells from a sample of blood, which comprises the steps of:
introducing a sample of blood into a blood separation device, the device including a collection tube, a first layer of a liquid density gradient material contained in the collection tube, a second layer of gel-like substance contained in the collection tube and situated above the first layer, and a porous foam member contained in the collection tube and situated above the second layer and in contact with the second layer, the second layer of gel-like substance being adapted to coat the portion of the porous foam member with which it is in contact and acting as a barrier between the first layer of liquid density gradient material and a blood sample introduced into the blood separation device, the liquid density gradient material of the first layer being formed with a specific gravity such that it is adapted to assume a position in the collection tube between the mononuclear cells and the heavier components of a blood sample placed in the tube after centrifugation of the tube; and
centrifuging the collection tube.

38. A method of manufacturing apparatus for separating mononuclear cells from blood, which comprises the steps of:
introducing a first layer of liqid density gradient material to a collection tube, the collection tube having a bottom closed end and an opposite top open end, the first layer of liquid density gradient material being situated at the bottom closed end of the collection tube;
introducing a second layer of a gel-like substance to the collection tube, the gel-like substance of the second layer having a specific gravity which is less than that of the liquid density gradient material of the first layer so that the second layer floats on top of the first layer;
introducing a porous foam member into the collection tube, the porous foam member being situated above the second layer of gel-like substance and in contact therewith; and
providing a sufficient free space above the porous foam member such that the collection tube is adapted to receive a blood sample.

39. A method as defined by claim 38, which further comprises the step of introducing one of an anti-coagulant and a stabilizing reagent into the collection tube, the one of the anti-coagulant and stabilizing reagent being situated above the porous foam member.

40. A method as defined by claim 38, which further comprises the step of heating the collection tube, the gel-like substance of the second layer becoming less viscous as the collection tube is heated such that it is adapted to be partially absorbed by the porous foam member with which it is in contact.

41. A method as defined by claim 38, which further comprises the step of introducing a third layer of Newtonian gel-like substance into the collection tube, the third layer being positioned above the porous foam member.

* * * * *